(12) United States Patent
Machado et al.

(10) Patent No.: US 9,480,790 B2
(45) Date of Patent: Nov. 1, 2016

(54) METHODS AND SYSTEMS FOR TREATING ACUTE HEART FAILURE BY NEUROMODULATION

(71) Applicant: The Cleveland Clinic Foundation, Cleveland, OH (US)

(72) Inventors: Sandra Machado, Beachwood, OH (US); Marc Penn, Beachwood, OH (US); Ali R. Rezai, Columbus, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/085,311

(22) Filed: Nov. 20, 2013

(65) Prior Publication Data

US 2014/0074069 A1    Mar. 13, 2014

Related U.S. Application Data

(63) Continuation of application No. 13/654,525, filed on Oct. 18, 2012, now Pat. No. 8,798,738, which is a continuation of application No. 12/185,473, filed on Aug. 4, 2008, now Pat. No. 8,818,501, which is a (Continued)

(51) Int. Cl.
*A61N 1/362* (2006.01)
*A61M 5/142* (2006.01)
*A61N 1/36* (2006.01)
(Continued)

(52) U.S. Cl.
CPC ........ *A61M 5/14212* (2013.01); *A61N 1/0565* (2013.01); *A61N 1/3627* (2013.01); *A61N 1/36114* (2013.01); *A61N 1/36585* (2013.01)

(58) Field of Classification Search
CPC .......... A61N 1/36585; A61N 1/0565; A61N 1/3627; A61N 1/36114; A61M 5/14212
USPC .............................................................. 607/2
See application file for complete search history.

(56) References Cited

U.S. PATENT DOCUMENTS

| 4,718,423 A | 1/1988 | Willis et al. |
| 4,947,866 A | 8/1990 | Lessar et al. |

(Continued)

FOREIGN PATENT DOCUMENTS

| CA | 2 848 781 | 3/2013 |
| EP | 1 871 469 | 10/2013 |

(Continued)

OTHER PUBLICATIONS

Ardell et al., "Differential sympathetic regulation of automatic, conductile, and contractile tissue in dog heart," American Journal of Physiology (Nov. 1988) 255 (5): H1050-H1059.

(Continued)

*Primary Examiner* — Alyssa M Alter
(74) *Attorney, Agent, or Firm* — Knobbe, Martens, Olson & Bear, LLP

(57) ABSTRACT

Methods of treating acute heart failure in a patient in need thereof. Methods include inserting a therapy delivery device into a pulmonary artery of the patient and applying a therapy signal to autonomic cardiopulmonary fibers surrounding the pulmonary artery. The therapy signal affects heart contractility more than heart rate. Specifically, the application of the therapy signal increases heart contractility and treats the acute heart failure in the patient. The therapy signal can include electrical or chemical modulation.

20 Claims, 7 Drawing Sheets

Related U.S. Application Data continuation of application No. 11/951,285, filed on Dec. 5, 2007, now abandoned.

(60) Provisional application No. 60/873,021, filed on Dec. 6, 2006.

(51) Int. Cl.
*A61N 1/05* (2006.01)
*A61N 1/365* (2006.01)

(56) References Cited

U.S. PATENT DOCUMENTS

| | | | |
|---|---|---|---|
| 4,950,227 A | 8/1990 | Savin et al. | |
| 5,067,957 A | 11/1991 | Jervis | |
| 5,156,154 A * | 10/1992 | Valenta et al. | 600/455 |
| 5,190,546 A | 3/1993 | Jervis | |
| 5,197,978 A | 3/1993 | Hess | |
| 5,213,098 A | 5/1993 | Bennett et al. | |
| 5,224,491 A | 7/1993 | Mehra | |
| 5,259,387 A | 11/1993 | DePinto | |
| 5,336,244 A | 8/1994 | Weijand | |
| 5,345,936 A | 9/1994 | Pomeranz et al. | |
| 5,365,926 A | 11/1994 | Desai | |
| 5,423,881 A | 6/1995 | Breyen et al. | |
| 5,431,649 A * | 7/1995 | Mulier | A61B 18/1477 600/374 |
| 5,564,434 A | 10/1996 | Halperin et al. | |
| 5,711,316 A | 1/1998 | Elsberry et al. | |
| 5,725,570 A | 3/1998 | Heath | |
| 5,755,766 A | 5/1998 | Chastain et al. | |
| 5,782,239 A | 7/1998 | Webster | |
| 5,853,411 A | 12/1998 | Whayne et al. | |
| 5,948,007 A | 9/1999 | Starkebaum et al. | |
| 5,954,761 A | 9/1999 | Machek et al. | |
| 5,968,040 A | 10/1999 | Swanson et al. | |
| 5,997,563 A | 12/1999 | Kretzers | |
| 6,036,697 A | 3/2000 | DiCaprio | |
| 6,038,480 A | 3/2000 | Hrdlicka et al. | |
| 6,058,331 A | 5/2000 | King | |
| 6,059,810 A | 5/2000 | Brown et al. | |
| 6,071,308 A | 6/2000 | Ballou et al. | |
| 6,136,021 A | 10/2000 | Tockman et al. | |
| 6,161,029 A | 12/2000 | Spreigl et al. | |
| 6,231,516 B1 | 5/2001 | Keilman et al. | |
| 6,241,724 B1 | 6/2001 | Fleischman et al. | |
| 6,266,564 B1 | 7/2001 | Hill et al. | |
| 6,292,695 B1 | 9/2001 | Webster et al. | |
| 6,295,475 B1 | 9/2001 | Morgan | |
| 6,319,241 B1 | 11/2001 | King et al. | |
| 6,353,762 B1 | 3/2002 | Baudino et al. | |
| 6,447,478 B1 | 9/2002 | Maynard | |
| 6,473,653 B1 | 10/2002 | Schallhorn et al. | |
| 6,522,926 B1 | 2/2003 | Kieval et al. | |
| 6,542,774 B2 | 4/2003 | Hill et al. | |
| 6,547,788 B1 | 4/2003 | Maguire et al. | |
| 6,564,096 B2 | 5/2003 | Mest | |
| 6,574,492 B1 | 6/2003 | Ben-Haim et al. | |
| 6,669,693 B2 | 12/2003 | Friedman | |
| 6,738,655 B1 | 5/2004 | Sen et al. | |
| 6,740,113 B2 | 5/2004 | Vrba | |
| 6,748,271 B2 | 6/2004 | Spinelli et al. | |
| 6,754,532 B1 | 6/2004 | Ferek-Petric | |
| RE38,654 E | 11/2004 | Hill et al. | |
| 6,832,478 B2 | 12/2004 | Anderson et al. | |
| 6,850,801 B2 | 2/2005 | Kieval et al. | |
| 6,912,419 B2 | 6/2005 | Hill et al. | |
| 6,985,774 B2 | 1/2006 | Kieval et al. | |
| 6,993,385 B1 | 1/2006 | Routh et al. | |
| 7,072,720 B2 | 7/2006 | Puskas | |
| 7,092,759 B2 | 8/2006 | Nehls et al. | |
| 7,096,070 B1 | 8/2006 | Jenkins et al. | |
| 7,158,832 B2 | 1/2007 | Kieval et al. | |
| 7,231,260 B2 | 6/2007 | Wallace et al. | |
| 7,260,431 B2 | 8/2007 | Libbus et al. | |
| 7,277,757 B2 | 10/2007 | Casavant et al. | |
| 7,277,761 B2 | 10/2007 | Shelchuk | |
| 7,279,007 B2 * | 10/2007 | Nikolic | A61B 17/12022 600/37 |
| 7,308,303 B2 | 12/2007 | Whitehurst et al. | |
| 7,389,149 B2 | 6/2008 | Rossing et al. | |
| 7,460,906 B2 | 12/2008 | Libbus | |
| 7,486,991 B2 | 2/2009 | Libbus et al. | |
| 7,499,742 B2 | 3/2009 | Bolea et al. | |
| 7,509,166 B2 | 3/2009 | Libbus | |
| 7,542,800 B2 | 6/2009 | Libbus et al. | |
| 7,547,286 B2 | 6/2009 | Choate | |
| 7,561,923 B2 | 7/2009 | Libbus et al. | |
| 7,616,997 B2 | 11/2009 | Kieval et al. | |
| 7,617,003 B2 | 11/2009 | Caparso et al. | |
| 7,623,926 B2 | 11/2009 | Rossing et al. | |
| 7,630,760 B2 | 12/2009 | Libbus et al. | |
| 7,634,317 B2 | 12/2009 | Ben-David et al. | |
| 7,643,875 B2 | 1/2010 | Heil, Jr. et al. | |
| 7,647,102 B2 | 1/2010 | Routh et al. | |
| 7,658,709 B2 | 2/2010 | Anderson et al. | |
| 7,706,884 B2 | 4/2010 | Libbus | |
| 7,734,348 B2 | 6/2010 | Zhang et al. | |
| 7,765,000 B2 | 7/2010 | Zhang et al. | |
| 7,769,446 B2 | 8/2010 | Moffitt et al. | |
| 7,801,614 B2 | 9/2010 | Rossing et al. | |
| 7,805,194 B1 | 9/2010 | Schecter | |
| 7,813,812 B2 | 10/2010 | Kieval et al. | |
| 7,840,271 B2 | 11/2010 | Kieval et al. | |
| 7,848,812 B2 | 12/2010 | Crowley et al. | |
| 7,869,881 B2 | 1/2011 | Libbus et al. | |
| 7,873,413 B2 | 1/2011 | McCabe et al. | |
| 7,881,782 B2 | 2/2011 | Libbus et al. | |
| 7,885,709 B2 | 2/2011 | Ben-David | |
| 7,885,711 B2 | 2/2011 | Ben-Ezra et al. | |
| 7,904,151 B2 | 3/2011 | Ben-David et al. | |
| 7,908,008 B2 | 3/2011 | Ben-David et al. | |
| 7,925,352 B2 | 4/2011 | Stack et al. | |
| 7,949,400 B2 | 5/2011 | Kieval et al. | |
| 8,000,793 B2 | 8/2011 | Libbus | |
| 8,005,545 B2 | 8/2011 | Ben-David et al. | |
| 8,014,874 B2 | 9/2011 | Rossing et al. | |
| 8,024,050 B2 | 9/2011 | Libbus et al. | |
| 8,027,724 B2 | 9/2011 | Wei et al. | |
| 8,032,215 B2 | 10/2011 | Libbus et al. | |
| 8,060,206 B2 | 11/2011 | Kieval et al. | |
| 8,086,314 B1 | 12/2011 | Kieval | |
| 8,121,693 B2 | 2/2012 | Libbus | |
| 8,126,560 B2 | 2/2012 | Schiener et al. | |
| 8,131,373 B2 | 3/2012 | Libbus | |
| 8,145,304 B2 | 3/2012 | Moffitt et al. | |
| 8,150,521 B2 | 4/2012 | Crowley et al. | |
| 8,155,744 B2 | 4/2012 | Rezai | |
| 8,175,705 B2 | 5/2012 | Libbus | |
| 8,195,289 B2 | 6/2012 | Heil, Jr. et al. | |
| 8,195,290 B2 | 6/2012 | Brockway et al. | |
| 8,204,591 B2 | 6/2012 | Ben-David et al. | |
| 8,229,564 B2 | 7/2012 | Rezai | |
| 8,244,355 B2 | 8/2012 | Bennett et al. | |
| 8,249,706 B2 | 8/2012 | Koh | |
| 8,290,595 B2 | 10/2012 | Kieval et al. | |
| 8,369,954 B2 | 2/2013 | Stack et al. | |
| 8,386,053 B2 | 2/2013 | Kornet | |
| 8,386,056 B2 | 2/2013 | Ben-David et al. | |
| 8,401,672 B2 | 3/2013 | Libbus et al. | |
| 8,406,877 B2 | 3/2013 | Smith et al. | |
| 8,412,326 B2 | 4/2013 | Arcot-Krishnamurthy et al. | |
| 8,417,354 B2 | 4/2013 | Zhang et al. | |
| 8,428,730 B2 | 4/2013 | Stack et al. | |
| 8,437,867 B2 | 5/2013 | Murney et al. | |
| 8,452,398 B2 | 5/2013 | Libbus et al. | |
| 8,473,076 B2 | 6/2013 | Libbus et al. | |
| 8,498,703 B2 | 7/2013 | Spinelli et al. | |
| 8,538,535 B2 | 9/2013 | Gross et al. | |
| 8,583,236 B2 | 11/2013 | Kieval et al. | |
| 8,606,359 B2 | 12/2013 | Rossing et al. | |
| 8,620,426 B2 | 12/2013 | Moffitt et al. | |
| 8,626,290 B2 | 1/2014 | Dagan et al. | |
| 8,626,299 B2 | 1/2014 | Gross et al. | |

(56) References Cited

U.S. PATENT DOCUMENTS

| | | |
|---|---|---|
| 8,634,921 B2 | 1/2014 | Chavan et al. |
| 8,639,332 B2 | 1/2014 | Kuhn et al. |
| 8,682,430 B2 | 3/2014 | Libbus et al. |
| 8,682,434 B2 | 3/2014 | Libbus |
| 8,712,531 B2 | 4/2014 | Kieval et al. |
| 8,718,789 B2 | 5/2014 | Bolea et al. |
| 8,725,250 B2 | 5/2014 | Brockway et al. |
| 8,755,907 B2 | 6/2014 | Kieval et al. |
| 8,788,066 B2 | 7/2014 | Cates et al. |
| 8,798,738 B2 | 8/2014 | Machado et al. |
| 8,805,501 B2 | 8/2014 | Libbus |
| 8,818,501 B2 | 8/2014 | Machado et al. |
| 8,838,246 B2 | 9/2014 | Kieval |
| 8,855,783 B2 | 10/2014 | Dagan et al. |
| 8,880,190 B2 | 11/2014 | Kieval et al. |
| 8,918,172 B2 | 12/2014 | Moffitt et al. |
| 8,929,990 B2 | 1/2015 | Moffitt et al. |
| 8,934,968 B2 | 1/2015 | Whitehurst et al. |
| 8,972,015 B2 | 3/2015 | Stack et al. |
| 8,983,601 B2 | 3/2015 | Fukamachi et al. |
| 9,005,100 B2 | 4/2015 | Gnanashanmugam et al. |
| 9,005,106 B2 | 4/2015 | Gross et al. |
| 9,031,650 B2 | 5/2015 | McCabe et al. |
| 9,031,669 B2 | 5/2015 | Zhang et al. |
| 9,044,609 B2 | 6/2015 | Bolea et al. |
| 9,067,071 B2 | 6/2015 | Sanders et al. |
| 9,126,048 B2 | 9/2015 | Ransbury et al. |
| 9,149,639 B2 | 10/2015 | Zhang et al. |
| 9,168,094 B2 | 10/2015 | Lee et al. |
| 9,216,289 B2 | 12/2015 | Libbus et al. |
| 2003/0114878 A1 | 6/2003 | Diederich et al. |
| 2004/0143254 A1 | 7/2004 | Vanney et al. |
| 2004/0172079 A1 | 9/2004 | Chinchoy |
| 2004/0260375 A1 | 12/2004 | Zhang et al. |
| 2005/0154321 A1* | 7/2005 | Wolinsky ............ A61B 5/0031 600/486 |
| 2005/0251239 A1* | 11/2005 | Wallace ................ A61N 1/057 607/126 |
| 2006/0058597 A1 | 3/2006 | Machado et al. |
| 2006/0074453 A1 | 4/2006 | Kieval et al. |
| 2006/0085046 A1 | 4/2006 | Rezai et al. |
| 2006/0206159 A1 | 9/2006 | Moffitt et al. |
| 2006/0229677 A1 | 10/2006 | Moffitt et al. |
| 2006/0259084 A1 | 11/2006 | Zhang et al. |
| 2006/0259085 A1 | 11/2006 | Zhang et al. |
| 2007/0135875 A1 | 6/2007 | Demarais et al. |
| 2008/0082137 A1 | 4/2008 | Kieval et al. |
| 2008/0167693 A1 | 7/2008 | Kieval et al. |
| 2008/0312711 A1 | 12/2008 | Struble |
| 2009/0018596 A1 | 1/2009 | Kieval |
| 2009/0163912 A1 | 6/2009 | Wang et al. |
| 2009/0228078 A1 | 9/2009 | Zhang et al. |
| 2009/0276022 A1 | 11/2009 | Burnes et al. |
| 2010/0222832 A1 | 9/2010 | Zhang et al. |
| 2011/0106199 A1 | 5/2011 | McCabe et al. |
| 2011/0160790 A1 | 6/2011 | Stegemann et al. |
| 2012/0310304 A1 | 12/2012 | Brockway et al. |
| 2013/0110208 A1 | 5/2013 | Inagaki et al. |
| 2013/0218221 A1 | 8/2013 | Zhang et al. |
| 2013/0253616 A1 | 9/2013 | Libbus et al. |
| 2013/0331919 A1 | 12/2013 | Zhang et al. |
| 2013/0338748 A1 | 12/2013 | Dagan |
| 2014/0052208 A1 | 2/2014 | Ransbury et al. |
| 2014/0114377 A1 | 4/2014 | Dagan et al. |
| 2014/0277235 A1 | 9/2014 | An et al. |
| 2014/0324115 A1 | 10/2014 | Ziegler et al. |
| 2015/0039058 A1 | 2/2015 | Masson et al. |
| 2015/0134019 A1 | 5/2015 | Moffitt et al. |
| 2015/0142011 A1 | 5/2015 | Cates et al. |
| 2015/0151121 A1 | 6/2015 | Dagan et al. |
| 2015/0238763 A1 | 8/2015 | Bolea et al. |

FOREIGN PATENT DOCUMENTS

| | | |
|---|---|---|
| EP | 2 316 525 | 1/2016 |
| WO | WO 97/24983 | 7/1997 |
| WO | WO 2006/007048 | 1/2006 |
| WO | WO 2008/054448 | 5/2008 |
| WO | WO 2009/135083 | 11/2009 |
| WO | WO 2012/149511 | 11/2012 |
| WO | WO 2015/179634 | 11/2015 |
| WO | WO 2016/040037 | 3/2016 |
| WO | WO 2016/040038 | 3/2016 |
| WO | WO 2016/111940 | 7/2016 |

OTHER PUBLICATIONS

Casadei, "Vagal control of myocardial . . . in humans," The Physiological Society (Mar. 2001): 817-823.

Ferrari et al., "Vagus nerve stimulation . . . future directions," Heart Fail Rev. (2011) 16: 195-203.

Klein et al., "Vagus nerve stimulation . . . heart failure," Cariology Journal (2010) 17 (6): 638-643.

Koizumi et al., "Functional significance of coactivation . . . ," National Academy of Sciences (Mar. 1982) 79 (6): 2116-2120.

Meyer et al., "Augmentation of left ventricular . . . ," Americ. Heart Assoc. (2010): 1286-1294.

Murphy, "Preliminary observations of the effects of simulation of . . . in man," CA Journal of Phys. And Pharmac (Jun. 1985). 63 (6): 649-655.

Randall et al., "Regional cardiac distribution . . . ," Federation Proceedings (Jul.-Aug. 1972) 31 (4): 1199-1208.

Randall, "Augmentor action to the sympathetic . . . ," Journal of Applied Physiology (Jul. 1960) 15 (4): 629-631.

Triposkiadis et al., "Sympathetic nervous . . . failure," Journal of Amer. Coll. of Cardiology (Nov. 3, 2009) 54 (19): 1747-1762.

Zarse, "Selective increase . . . sympathetic tone," Journal of Amer. Coll. of Cardiology (2005) 46 (7): 1355-1359.

International Search Report for related International Application No. PCT/US2007/025166 mailed on Mar. 10, 2008.

Written Opinion for related International Application No. PCT/US2007/025166 mailed on Mar. 10, 2008.

International Preliminary Report on Patentability for related International Application No. PCT/US2007/025166 mailed on Jun. 10, 2009.

Extended European Search Report for EP 07853308.0 dated Apr. 16, 2010.

Rudski et al., "Guidelines for the Echocardiographic Assessment of the Right Heart in Adults: A Report from the American Society of Echocardiography", J Am Soc Echocardiogr, 2010, vol. 23, pp. 685-713.

Lawo et al., "Electrical Signals Applied During the Absolute Refractory Period", JACC, Dec. 20, 2005, vol. 46, No. 21, pp. 2229-2236.

* cited by examiner ic cardiopulmonary fiber surrounding the pulmonary trunk to treat the acute heart failure. The at least one sympathetic cardiopulmonary fiber affects heart contractility more than heart rate.

METHODS AND SYSTEMS FOR TREATING ACUTE HEART FAILURE BY NEUROMODULATION

CROSS-REFERENCE TO RELATED APPLICATIONS

This application is a continuation of U.S. application Ser. No. 13/654,525, filed on Oct. 18, 2012 and issued as U.S. Pat. No. 8,798,738 on Aug. 5, 2014, which is a continuation of U.S. application Ser. No. 12/185,473, filed on Aug. 4, 2008 and issued as U.S. Pat. No. 8,818,501 on Aug. 26, 2014, which is a continuation of U.S. application Ser. No. 11/951,285, filed on Dec. 5, 2007, which claims priority to U.S. Provisional Application No. 60/873,021, filed on Dec. 6, 2006, each of U.S. application Ser. No. 12/185,473, U.S. application Ser. No. 11/951,285, and U.S. Provisional Application No. 60/873,021 being incorporated by reference in its entirety herein. The present application is also related to U.S. application Ser. No. 11/222,766, filed on Sep. 12, 2005, which is incorporated by reference herein.

FIELD OF THE INVENTION

The present invention relates to methods and systems for treating acute heart failure by electrically modulating autonomic cardiopulmonary fibers.

BACKGROUND OF THE INVENTION

Diseases or injuries causing or resulting in acute heart failure are widespread. The goals of therapy in acute heart failure are often to correct the hemodynamic instability and address decompensation in order to increase patient mortality. One treatment option for acute heart failure is the administration of inotropic agents, such as dopamine and dobutamine. However, inotropic agents have both chronotropic and inotropic effects and characteristically increase heart contractility at the expense of significant increments in oxygen consumption secondary to elevations in heart rate. As a result, although these inotropic agents increase myocardial contractility and improve hemodynamics, clinical trials have consistently demonstrated excess mortality caused by cardiac arrhythmias and increase in the myocardium consumption.

As such, there is a need for a method of selectively and locally treating acute heart failure and otherwise achieving hemodynamic control without causing untoward systemic effect.

SUMMARY OF THE INVENTION

The present invention provides methods for treating medical conditions by transvascular neuromodulation of a target site of an autonomic nervous system. The methods of the present invention for treating medical conditions encompass neuromodulation of any combination of one or more target sites of the autonomic nervous system. Non-limiting examples of medical conditions that can be treated according to the present invention include cardiovascular medical conditions.

In an embodiment, the present invention provides a method of treating acute heart failure in a patient in need thereof comprising inserting a delivery device into a pulmonary artery and positioning the delivery device at a pulmonary trunk of the pulmonary artery. The method also comprises applying a therapy signal to at least one sympathetic cardiopulmonary fiber surrounding the pulmonary trunk to treat the acute heart failure. The at least one sympathetic cardiopulmonary fiber affects heart contractility more than heart rate.

In another embodiment, the present invention provides a system for treating acute heart failure comprising a delivery device for positioning in the pulmonary artery at the pulmonary trunk. The system further includes a controller in communication with the delivery device for enabling the delivery device to apply a therapy signal to at least one sympathetic cardiopulmonary fiber surrounding the pulmonary trunk to treat acute heart failure. The at least one sympathetic cardiopulmonary fiber affects heart contractility more than heart rate.

DETAILED DESCRIPTION OF THE INVENTION

Figure 1:
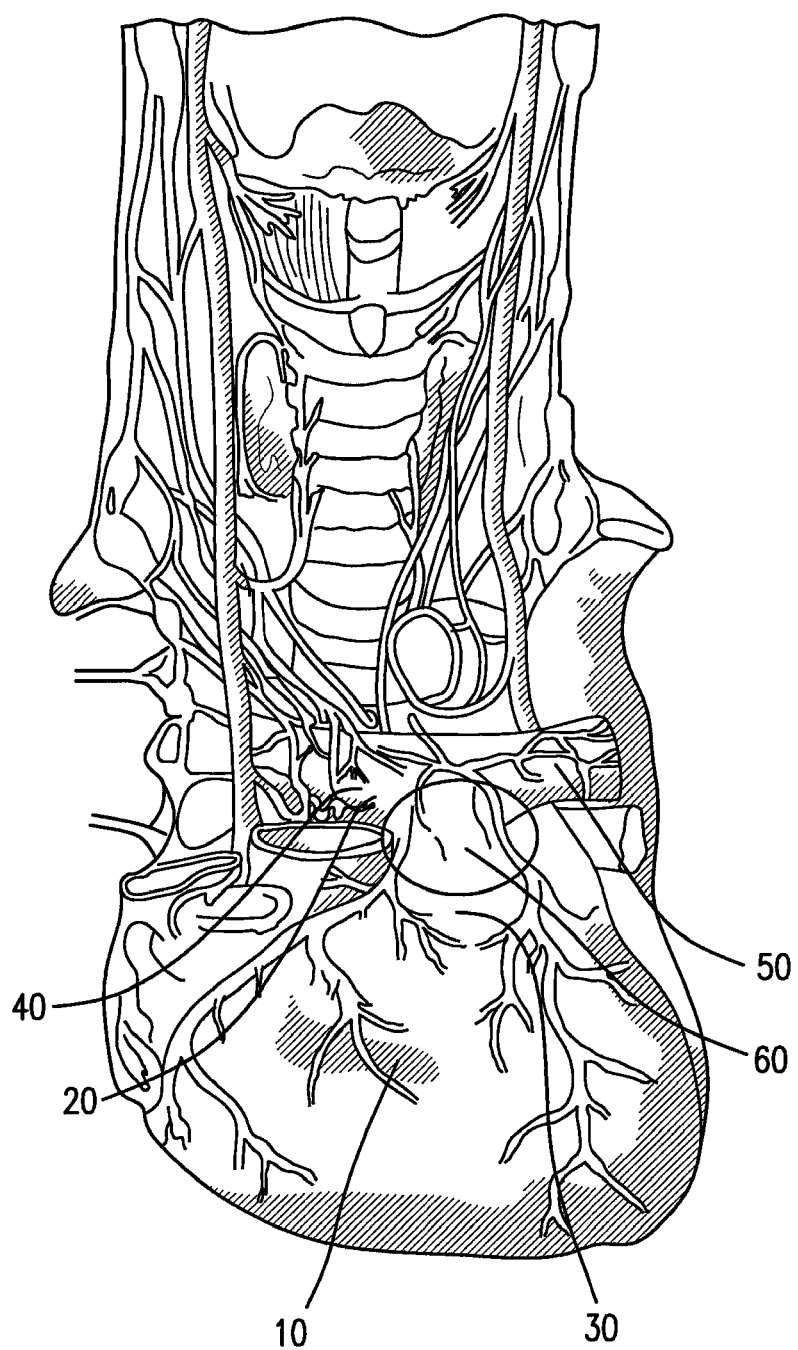
FIG. 1 is a schematic illustration of the heart and surrounding areas, showing the stimulation sites according to the present invention.

The present invention provides methods for treating medical conditions by transvascular neuromodulation of a target site of an autonomic nervous system. The methods of the present invention for treating medical conditions encompass neuromodulation of any combination of one or more target sites of the autonomic nervous system. Non-limiting examples of medical conditions that can be treated according to the present invention include cardiovascular medical conditions.

With respect to treating cardiovascular medical conditions, such medical conditions can involve any medical conditions related to the components of the cardiovascular system such as, for example, the heart and aorta. Non-limiting examples of cardiovascular conditions include post-infarction rehabilitation, shock (hypovolemic, septic, neurogenic), valvular disease, heart failure, angina, microvascular ischemia, myocardial contractility disorder, cardiomyopathy, hypertension including pulmonary hypertension and systemic hypertension, orthopnea, dyspenea, orthostatic hypotension, dysautonomia, syncope, vasovagal reflex, carotid sinus hypersensitivity, pericardial effusion, heart failure, and cardiac structural abnormalities such as septal defects and wall aneurysms. Non-limiting examples of vessels into which therapy delivery devices, according to the present invention, are positioned to access autonomic target sites innervating components of the cardiovascular system are the carotid arteries; aorta; superior vena cava; inferior vena cava; pulmonary veins and arteries; carotid arteries; and subclavian arteries and veins. In a preferred embodiment, a therapy delivery device is used in conjunction with a pulmonary artery catheter, such as a Swan-Ganz type pulmonary artery catheter to delivery transvascular neuromodulation via the pulmonary artery to an autonomic target site to treat a cardiovascular condition according to the present invention. Specifically, in this preferred embodiment, a therapy delivery device is housed within one of the multiple vessels of a pulmonary artery catheter.

The present invention provides systems and methods for treating acute heart failure, also known as decompensated heart failure, by modulating at least one sympathetic cardiopulmonary fiber that affects heart contractility more than heart rate. In a preferred embodiment, a plurality of sympathetic cardiopulmonary fibers is modulated that collectively affect heart contractility more than heart rate. The fibers can be modulated by chemical and/or electrical modulation (including ablation) and the modulation includes stimulating and/or inhibiting the fibers. In the case of chemical modulation, bioactive agents may be used, including neurotransmitter mimics; neuropeptides; hormones; prohormones; antagonists, agonists, reuptake inhibitors, or degrading enzymes thereof, peptides; proteins; therapeutic agents; amino acids; nucleic acids; stem cells, or any combination thereof and may be delivered by a slow release matrix or drug pump.

According to the methods of the present invention, a delivery device, which can be an electrode in the case of electrical modulation, or a drug delivery device (e.g., a catheter) in the case of chemical modulation, is inserted into the pulmonary artery and positioned at a location within the pulmonary trunk such that activation of the delivery device at that location results in selective modulation of sympathetic cardiopulmonary fibers. Specifically, the sympathetic cardiopulmonary fibers that are modulated collectively affect heart contractility more than heart rate. Preferably, the delivery device is positioned at a site within the pulmonary artery such that activation of the delivery device results in the greatest effect on heart contractility and the least effect on heart rate and/or oxygen consumption compared to activation of the delivery device at any other site in the pulmonary artery. In certain embodiments, the effect on heart contractility is to increase heart contractility. In certain embodiments, electrical modulation is provided in combination with chemical modulation. In such embodiments, the present invention also provides systems that include electrical and chemical delivery devices.

FIG. 1 is a schematic illustration of the heart 10 and the pulmonary artery 20. As is known in the art, the pulmonary artery includes the pulmonary trunk 30, which begins at the base of the right ventricle; the right pulmonary artery 40; and the left pulmonary artery 50. The pulmonary trunk is short and wide, approximately 5 cm (2 inches) in length and 3 cm (1.2 inches) in diameter. In a preferred embodiment, an electrical delivery device is activated at the site 60 of the pulmonary trunk 30 that is at the base of the T-shape (circled in FIG. 1) formed by the left branch and right branch of the pulmonary artery.

Figure 2:
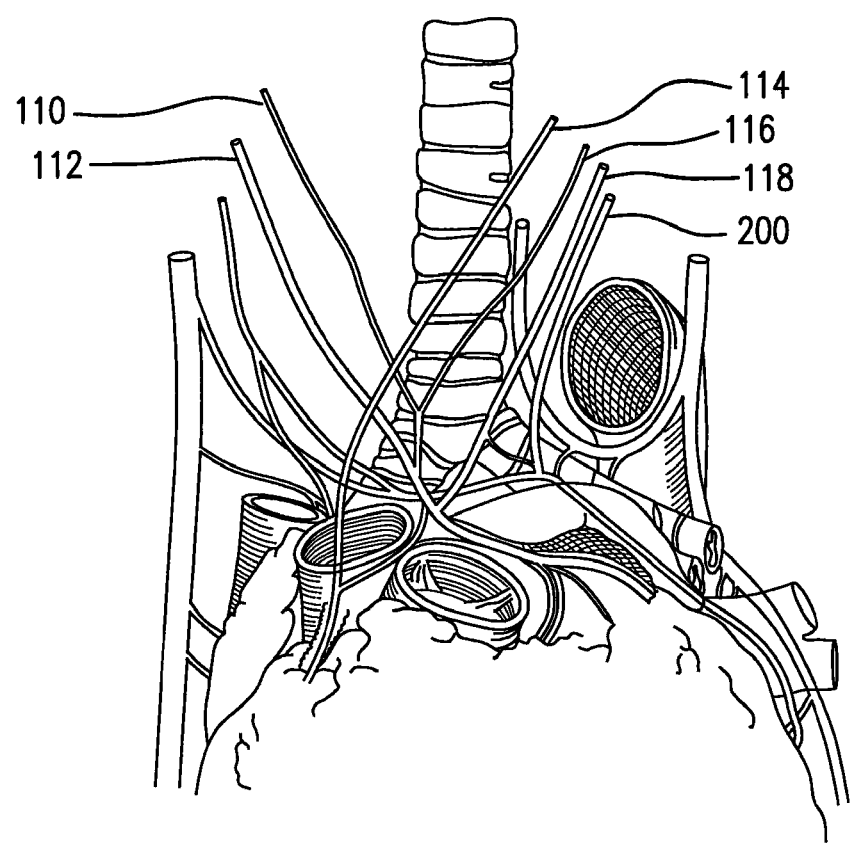
FIG. 2 is a schematic illustration of the specific nerves where stimulation can be applied according to an embodiment of the present invention.

The neuromodulation of the present invention is accomplished by applying a therapy signal, such as an electrical and/or chemical signal to the pulmonary trunk, such as at least one of the anterior wall, the posterior wall, the superior wall, and the lateral wall. The therapy signal is thereby applied to the sympathetic cardiopulmonary fibers, or nerves, surrounding the pulmonary trunk. These sympathetic fibers can include the right sympathetic cardiopulmonary nerves and the left sympathetic cardiopulmonary nerves, as illustrated in FIG. 2. The right sympathetic cardiopulmonary nerves include the right dorsal medial cardiopulmonary nerve 110 and the right dorsal lateral cardiopulmonary nerve 112. The left sympathetic cardiopulmonary nerves include the left ventral cardiopulmonary nerve 114, the left dorsal medial cardiopulmonary nerve 116, the left dorsal lateral cardiopulmonary nerve 118, and the left stellate cardiopulmonary nerve 200.

The delivery device can be introduced by any route or means to access the pulmonary artery. For example, the delivery device can be introduced through a large vein, such as the internal jugular, subclavian, or femoral veins or an artery and can be threaded, perhaps with the aid of fluoroscopy, into the pulmonary artery and placed at the pulmonary trunk.

The present invention also provides systems for treating acute heart failure. In an embodiment, the system includes a delivery device, which can be an electrical and/or chemical delivery device (such as an electrode and/or catheter) for positioning in the pulmonary artery at the pulmonary trunk and a controller, such as a pulse generator when an electrical delivery device is used and a drug pump when a chemical delivery device is used, in communication with the delivery device for enabling the delivery device to apply a therapy signal to at least one sympathetic cardiopulmonary fiber surrounding the pulmonary trunk to treat acute heart failure, wherein said at least one sympathetic cardiopulmonary fiber affects heart contractility more than heart rate. In certain embodiments, the system further includes a sensor for measuring cardiac parameters and generating a sensor signal.

Figure 3:
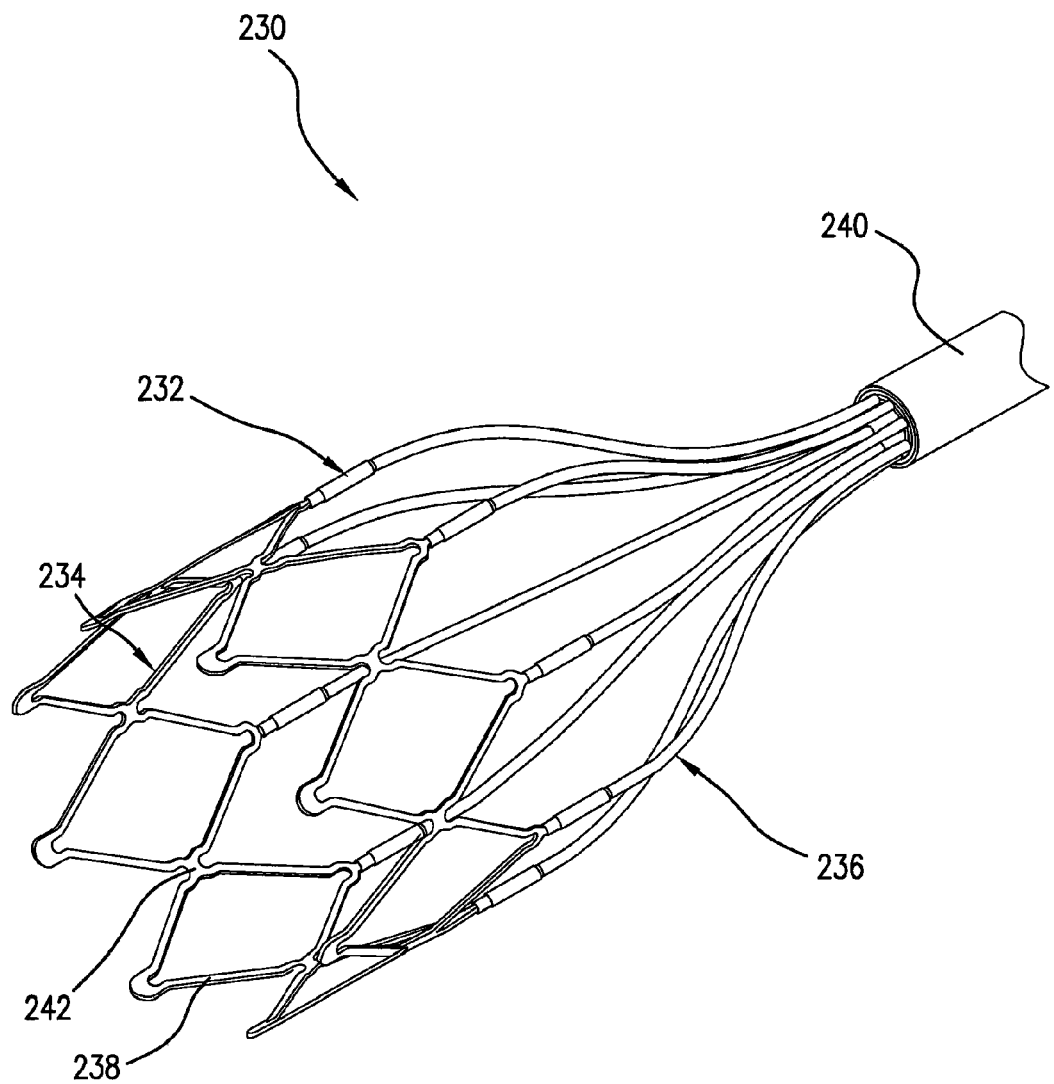
FIG. 3 is an electrical delivery device to be positioned within the pulmonary artery according to an embodiment of the present invention.

FIG. 3 provides an illustration of an exemplary electrical delivery device that can be used in accordance with an embodiment of a system of the present invention when electrical modulation is desired. The electrical delivery device is an intraluminal electrode assembly 230 that can provide intimate contact with a vessel wall. The intraluminal electrode assembly 230 includes a plurality of insulated electrical conductors 236, each conductor 236 connected to a preferably cylindrical electrode 232 disposed annularly thereon. There can be any number of conductors 236 having any number of electrodes 232 disposed thereon, but in a preferred embodiment, there are eight conductors with each conductor have one electrode disposed thereon. A frame 234 is connected to the ends of the plurality of insulated electrical conductors 236. In certain embodiments, electrodes 232 serve as cathodes and frame 234 serves as an anode.

Frame 234 is collapsible for fitting within a catheter lumen 240 during insertion into the body. Specifically, frame 234 has a first collapsed configuration smaller than the diameter of lumen 240 and, when deployed, a second radially expanded configuration designed to contact the vessel wall against which intraluminal electrode assembly 230 is positioned. Frame 234 is preferably fabricated from a super-elastic material, such as nitinol, for example, which allows frame 234 to return to its expanded state when deployed from lumen 240 and assume a collapsed state when retracted back into lumen 240. In a preferred embodiment, the distal end of frame 234 has an open stent-like configuration, preferably a plurality of diamond shapes 238 connected to each other by connector 242, creating a closed circular loop. Although electrodes 232 can be mounted at any position on insulated conductor 236, they are preferably mounted near frame 234.

In a preferred embodiment, lumen 240 is one lumen of a multi-lumen pulmonary catheter as described in more detail in co-pending application Ser. No. 11/222,774, filed on Sep. 12, 2005.

Electrical delivery device 230 is connected via a stimulation lead/catheter to a controller (not shown). The electrical delivery device may be placed temporarily in the pulmonary trunk adjacent to a sympathetic cardiopulmonary fiber. The controller of an embodiment of a system of the present invention is used to operate and supply power to the delivery device and enable the delivery device to deliver a therapy signal to a sympathetic cardiopulmonary fiber. The controller may be powered by a battery (which can be rechargeable), an external power supply, or a fuel cell. The controller may also be integral with the delivery device (such as a single stimulation lead/power generator or a single catheter/drug delivery pump). In the case of electrical modulation, the controller may change the output to the electrode by way of polarity, pulse width, amplitude, frequency, voltage, current, intensity, duration, wavelength, and/or waveform. The controller may operate any number or combination of electrodes. In the case of chemical modulation, the controller may change the dosage, timing or other parameters of drug delivery. The controller may operate any number of combination of drug ports. The controller can be external to the patient's body for use by the attending physician to program the controller and to monitor its performance or internal to the patient's body.

In the case of electrical modulation, the controller activates the electrical delivery device to initiate or adjust application of an electrical signal including terminating, increasing, decreasing, or changing the rate or pattern of a pulsing parameter. The controller also enables an electrical delivery device to deliver an electrical signal that may be episodic, continuous, phasic, in clusters, intermittent, upon demand by the patient or medical personnel, or preprogrammed to respond to a sensor. Preferably, the oscillating electrical signal is operated at a voltage between about 0.1 microvolts to about 20 V. More preferably, the oscillating electrical signal is operated at a voltage between about 1 V to about 15 V. For microstimulation, it is preferable to stimulate within the range of 0.1 microvolts to about 1 V. Preferably, the electric signal source is operated at a frequency range between about 2 Hz to about 2500 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the electrode is monopolar; bipolar when the electrode is bipolar; and multipolar when the electrode is multipolar. The waveform may be, for example, biphasic square wave, sine wave, or other electrically safe and feasible combinations. The electrical signal may be applied to multiple target sites simultaneously or sequentially.

In the case of chemical modulation, the controller can enable a drug port to deliver a bioactive agent to the target site. Where chemical and electrical modulation are both used, the controller can also coordinate delivery of the bioactive agent with the electrical neuromodulation (e.g., delivery of the bioactive agent prior to, concurrent with, or subsequent to electrical neuromodulation). The delivery of the bioactive agent maybe continuous, intermittent, chronic, phasic, or episodic.

An open-loop or closed-loop feedback mechanism may be used in conjunction with any of the methods of the present invention. In an open-loop feedback mechanism, a professional can monitor cardiac parameters of the patient and accordingly adjust the therapy signal applied to sympathetic cardiopulmonary fiber. Non-limiting examples of cardiac parameters monitored include arterial blood pressure, central venous pressure, capillary pressure, systolic pressure variation, arterial blood gases, cardiac output, systemic vascular resistance, pulmonary artery wedge pressure, and mixed venous oxygen saturation. Cardiac parameters can be monitored by an electrocardiogram, invasive hemodynamics, an echocardiogram, or blood pressure measurement or other devices known in the art to measure cardiac function. Other parameters such as body temperature and respiratory rate can also be monitored and processed as part of the feedback mechanism.

In a closed-loop feedback mechanism, the cardiac parameters are processed by at least one sensor and the neuromodulation is continuously adjusted according to the output generated by the sensor. Specifically, a sensor detects a cardiac parameter and generates a sensor signal. The sensor signal is processed by a sensor signal processor that provides a control signal to a signal generator. The signal generator, in turn, generates a response to the control signal by activating or adjusting the therapy signal applied by the delivery device to a sympathetic cardiopulmonary fiber. The control signal may be an indication to initiate, terminate, increase, decrease or change the rate or pattern of a pulsing or dosing parameter of the neuromodulation and the response to the control signal can be the respective initiation, termination, increase, decrease or change in rate or pattern of the respective pulsing or dosing parameter. The processing of closed-loop feedback systems for electrical neuromodulation is described in more detail in respective U.S. Pat. Nos. 6,058,331 and 5,711,316, both of which are incorporated by reference herein.

Figure 4:
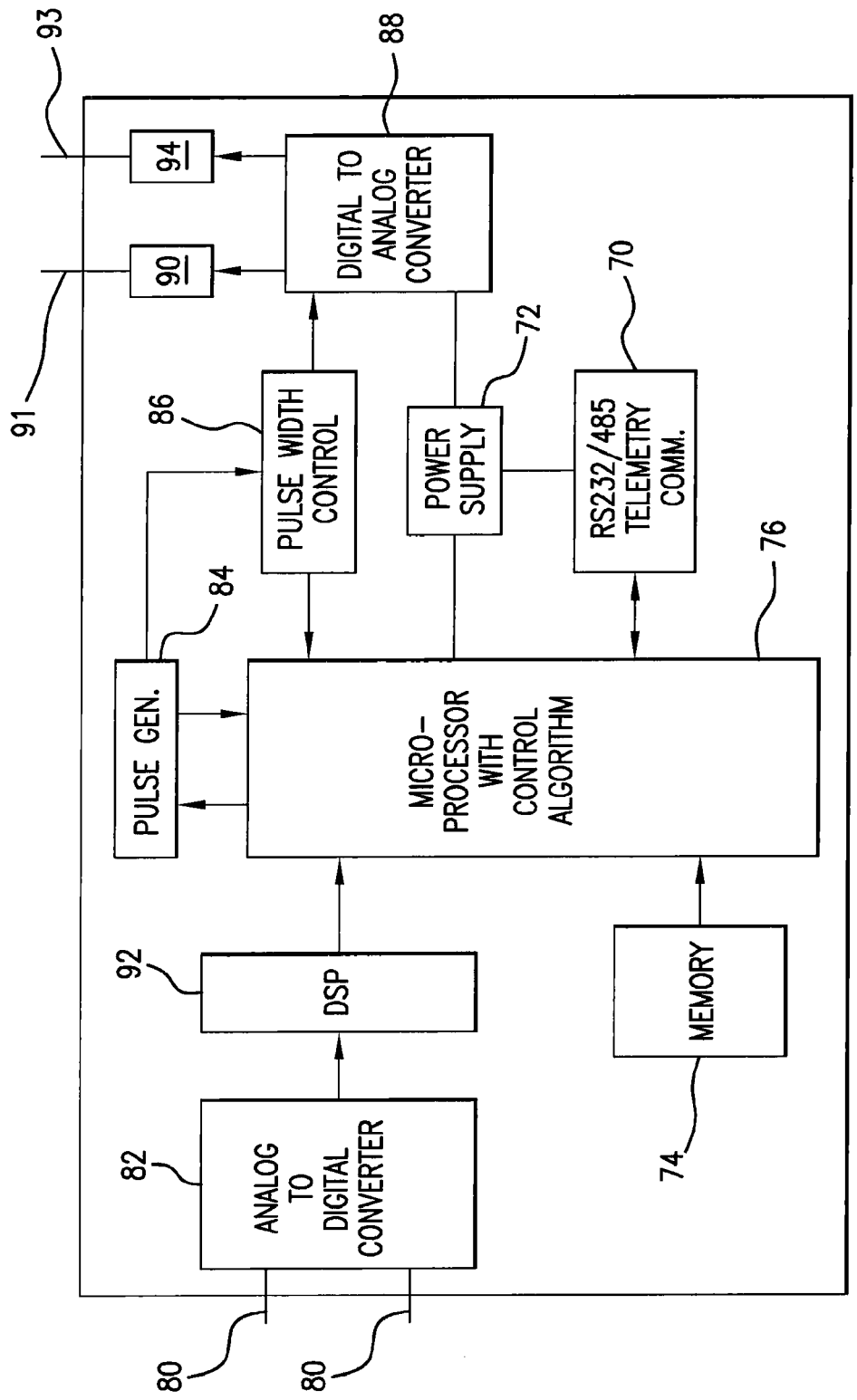
FIG. 4 is a schematic illustration of the components used in a controller of an embodiment of a system of the present invention.

Closed-loop electrical modulation, according to the present invention can be achieved by a modified form of an implantable SOLETRA, KINETRA, RESTORE, or SYN-ERGY signal generator available from Medtronic, Minneapolis, Minn. as disclosed in U.S. Pat. No. 6,353,762, the teaching of which is incorporated herein in its entirety, a controller as described in FIG. 4, or utilization of CIO DAS 08 and CIO-DAC 16 I processing boards and an IBM compatible computer available from Measurement Computing, Middleboro, Mass. with Visual Basic software for programming of algorithms. Such controllers can be modified for external, as opposed to implantable use. With reference to FIG. 4, an illustration of a non-limiting example of a controller comprising a microprocessor 76 such as an MSP430 microprocessor from Texas Instruments Technology, analog to digital converter 82 such as AD7714 from Analog Devices Corp., pulse generator 84 such as CD1877 from Harris Corporation, pulse width control 86, lead driver 90, digital to analog converter 88 such as MAX538 from Maxim Corporation, power supply 72, memory 74, and communications port or telemetry chip 70 are shown. Optionally, a digital signal processor 92 is used for signal conditioning and filtering. Input leads 78 and 80 and output leads 91 and 93 are also illustrated. Additional stimulation leads, sensors, and chemical delivery devices may be added to the controller as required. As a non-limiting example, inputs from sensors, such as a pulmonary artery wedge pressure sensor, are input to analog to digital converter 82. Microprocessor 76 receiving the sensor inputs uses algorithms to analyze the cardiac parameter of the patient and using PID, Fuzzy logic, or other algorithms, computes an output to pulse generator drivers 90 and 94, respectively, to neuromodulate the target site where the delivery devices are placed. The output of analog to digital converter 82 is connected to microprocessor 76 through a peripheral bus including address, data and control lines. Microprocessor 76 processes the sensor data in different ways depending on the type of transducer in use. When the signal on the sensor indicates a cardiac parameter outside of threshold values, for example reduced pulmonary artery wedge pressure, programmed by the clinician and stored in a memory, the therapy signal applied through output drivers 90 and 94 of the controller will be adjusted. The output voltage or current from the controller are then generated in an appropriately configured form (voltage, current, frequency), and applied to the one or more delivery devices placed at the target site for a prescribed time period to elevated the pulmonary artery wedge pressure. If the patient's pulmonary artery wedge pressure as monitored by the system is not outside of the normal threshold limits, or if the controller output (after it has timed out) has resulted in a correction of the pulmonary artery wedge pressure to within a predetermined threshold range, no further therapy signal is applied to the target site and the controller continues to monitor the patient via the sensors. A block diagram of an algorithm which may be used in the present invention is shown in FIG. 3.

Figure 5:
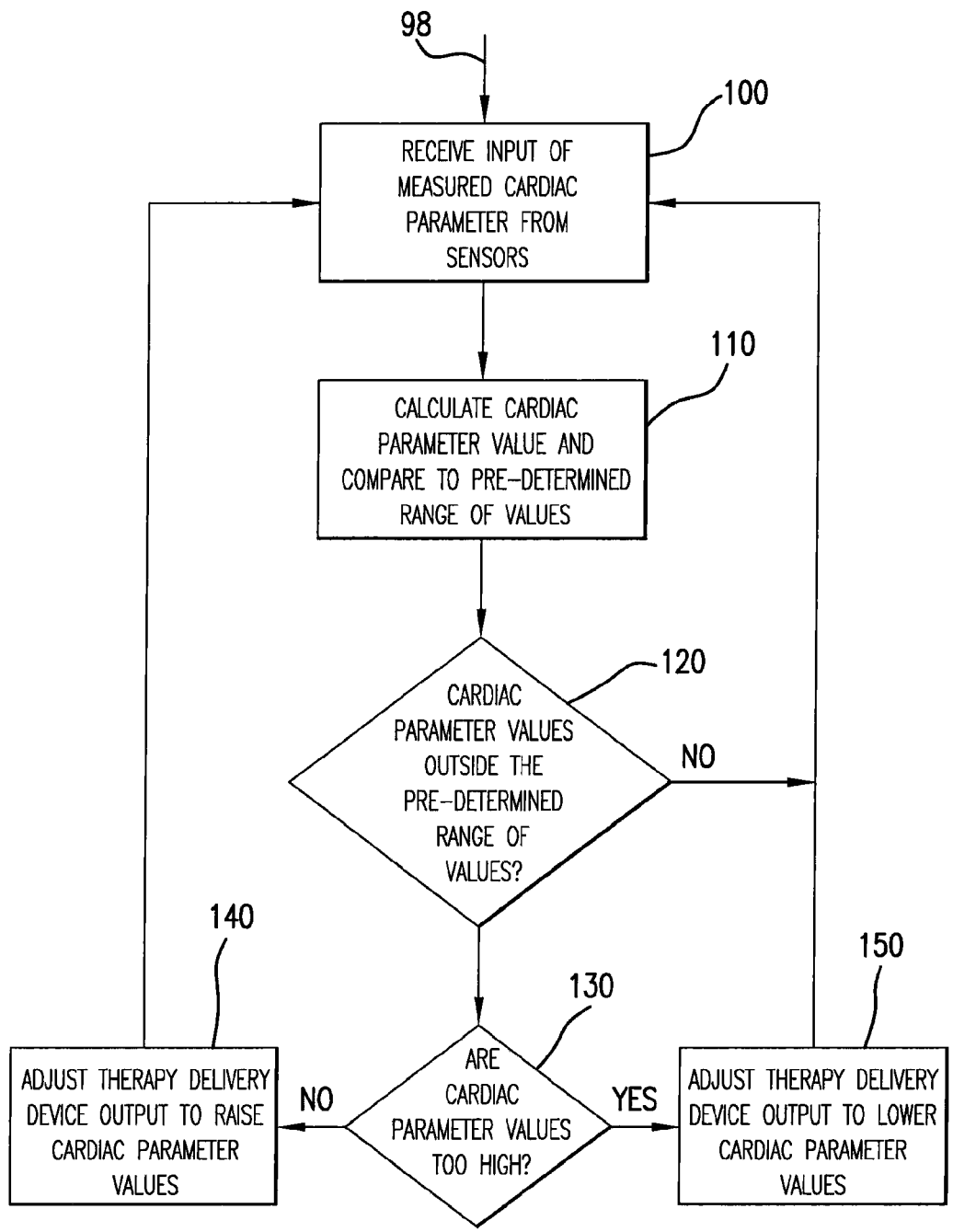
FIG. 5 is a block diagram of an algorithm to determine action taken by a controller microprocessor in response to sensor input according to an embodiment of a system of the present invention.

Referring to FIG. 5, suitably conditioned and converted sensor data 98 can be input to the algorithm in block 100. The program can compute at least one value of at least one cardiac parameter such as, for example pulmonary artery wedge pressure or cardiac output, and compares the measured value of the cardiac parameter to a pre-determined range of values, which is determined in advance to be the desired therapeutic range of values. This range can be programmed into the microprocessor via the telemetry or communications port of the controller. The algorithm can compare 110, and then can determine whether or not the measured value lies outside the pre-determined range of values 120. If the measured cardiac parameter value is not outside the pre-determined range of values, the program can continue to monitor the sensors and reiterates the comparison part of the algorithm. If the measured cardiac parameter value is outside of the pre-determined range of values, a determination or comparison can be made 130, as to whether the value is too high or too low compared with the pre-determined range. If the cardiac parameter value is too high, an adjustment to the delivery device can be made 150, to lower the cardiac parameter value of the patient by calculating an output signal for the pulse generator or drug delivery device to deliver a sufficient amount of the pharmaceutical or electrical modulation to lower the cardiac parameter of the patient. The algorithm can continue to monitor the cardiac parameter following the adjustment. If the cardiac parameter value is too low then an adjustment to the delivery device can be made 140, to raise the cardiac parameter value by calculating an output signal for the pulse generator or drug delivery device to deliver a sufficient amount of a pharmaceutical or electrical modulation to raise the cardiac parameter value of the patient. The algorithm can continue to monitor the cardiac parameter of the patient 100, following the adjustment. The amount of adjustment made may be determined by proportional integral derivative algorithms of by implementation of Fuzzy logic rules. Of course, the above-described sensory system is just exemplary and other ways of processing sensory data can be utilized.

With respect to the control of specific electrical parameters, the stimulus pulse frequency may be controlled by programming a value to a programmable frequency generator using the bus of the controller. The programmable frequency generator can provide an interrupt signal to the microprocessor through an interrupt line when each stimulus pulse is to be generated. The frequency generator may be implemented by model CDP1878 sold by Harris Corporation. The amplitude for each stimulus pulse may be programmed to a digital to analog converter using the controller's bus. The analog output can be conveyed through a conductor to an output driver circuit to control stimulus amplitude. The microprocessor of the controller may also program a pulse width control module using the bus. The pulse width control can provide an enabling pulse of duration equal to the pulse width via a conductor. Pulses with the selected characteristics can then be delivered from signal generator through a cable and lead to the target site or to a device such as a proportional valve or pump. The microprocessor can execute an algorithm to provide modulation of a target site with closed loop feedback control. For some types of sensors, a microprocessor and analog to digital converter will not be necessary. The output from sensor can be filtered by an appropriate electronic filter in order to provide a control signal for signal generator. An example of such a filter is found in U.S. Pat. No. 5,259,387 "Muscle Artifact Filter," issued to Victor de Pinto on Nov. 9, 1993, incorporated herein by reference in its entirety. Of course, the specific electrical and/or chemical parameters can be controlled in other ways as well.

EXAMPLES

Example 1

Six open-chest dogs were instrumented with a left ventricle conductance catheter and an aortic flow probe. Modified electrode-catheters were placed inside the pulmonary artery under echocardiographic and fluoroscopic guidance in five dogs. In the last dog, a stent-based electrode, as illustrated in FIG. 3, was used. Stimulation was applied at 20 Hz, 0.4 ms, and 15-25 mA. The corresponding hemodynamic effects are reported as averages of 30 second periods of continuous recording.

Pressure variation in the left ventricle over time increased in all dogs. The average increment was 25.7% (+/−11.8) and the average of maximum increase variation was 28.3 (+/−8.9). Emax was measured in the last animal, showing a 45% increase. The average reduction of RR interval during stimulation was 3.3% (+/−10.4).

Therefore, electrical modulation via a pulmonary artery catheter can produce positive inotropic effects with minimal changes in heart rate.

Example 2

Eight open-chest dogs are instrumented with a left ventricle conductance catheter and an aortic flow probe. Modified electrode-catheters are placed inside the pulmonary artery under echocardiographic and fluoroscopic guidance in five dogs. In three dogs, a stent-based electrode, as illustrated in FIG. 3, is used. Stimulation is applied at 20 Hz, 0.4 ms, and 15-25 mA. The corresponding hemodynamic effects are reported as averages of 30 second periods of continuous recording.

Figure 6:
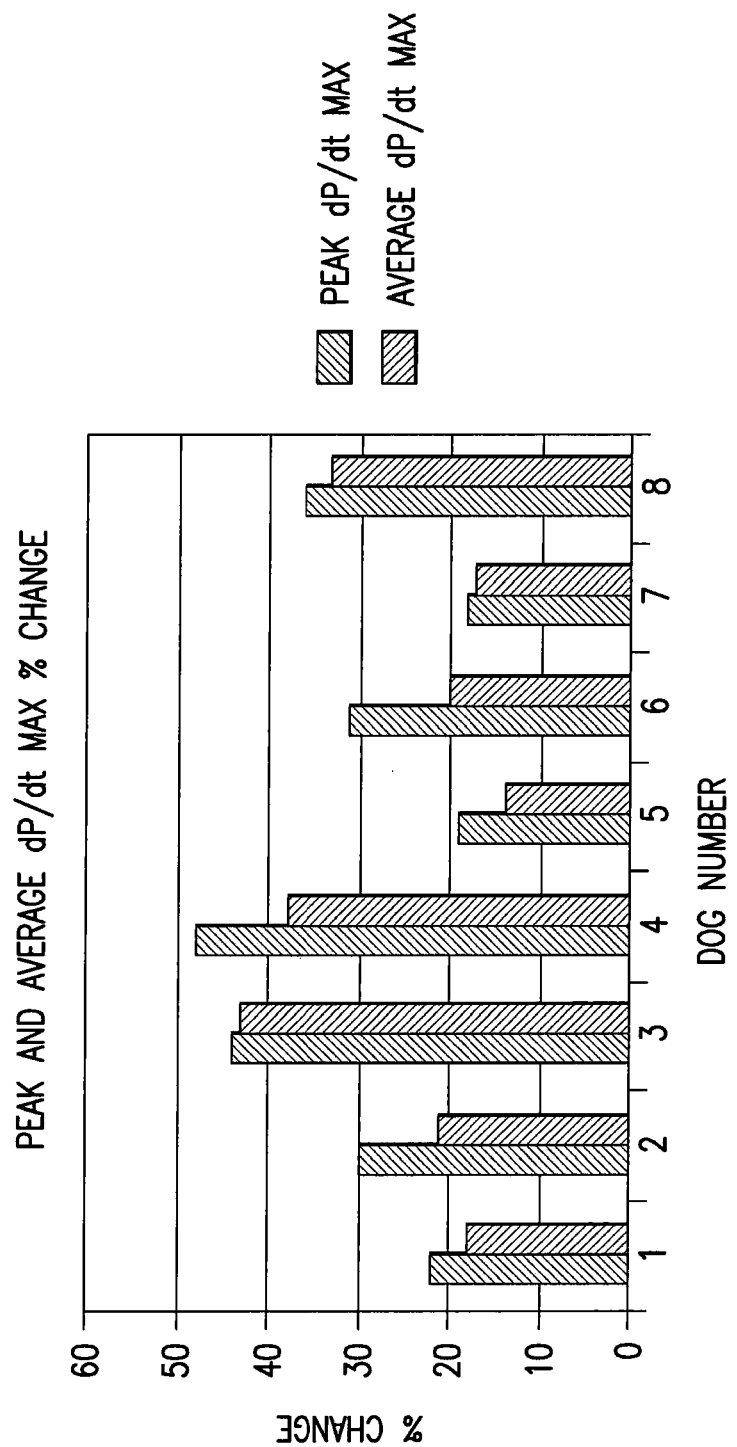
FIG. 6 is a graph showing the peak and average contractility percentage changes in dogs treated with electrical modulation according to an embodiment of the present invention and as described in Example 1.

FIG. 6 shows the percentage changes in dP/dt max for each dog when compared to the baseline. Specifically, FIG. 6 shows the peak dP/dt max % change achieved during modulation and the average % change in dP/dt max in a period of 30 seconds. There is significant increase in dP/dt max during modulation ranging from 21-22 to 44-45%. However, there is no significant change between the average and the peak value.

Figure 7:
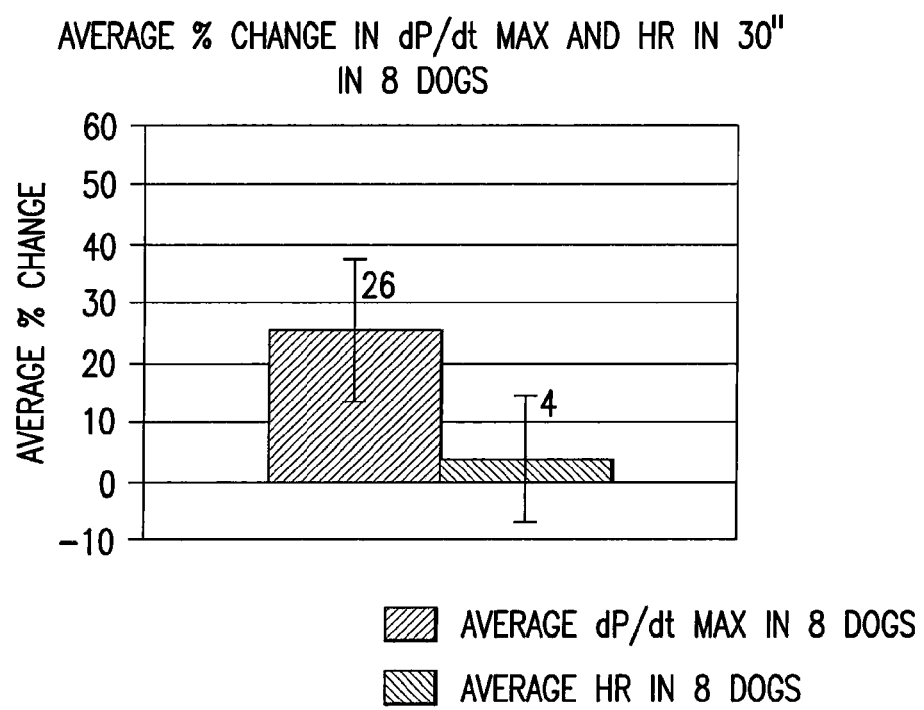
FIG. 7 is a graph showing the average percentage change in contractility compared to heart rate in dogs treated with electrical modulation according to an embodiment of the present invention and as described in Example 1.

FIG. 7 compares the average dP/dt max to the percentage increase in heart rate in the eight dogs. As shown, the heart rate increase is minimal when compared to increase in heart contractility (dP/dt max).

The foregoing description and examples has been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

The invention claimed is:

1. A therapy delivery device for treating cardiovascular medical conditions, comprising:
   a plurality of insulated electrical conductors each having a distal end;
   a plurality of electrodes, each said electrode of the plurality of electrodes being in electrical communication with one said insulated electrical conductor of plurality of insulated electrical conductors;
   a collapsible frame connected to the distal ends of the plurality of insulated electrical conductors, the collapsible frame defining a closed circular loop joined by a plurality of connectors, the plurality of electrodes proximal to the collapsible frame;
   the collapsible frame configured to expand from a first position when positioned within a catheter lumen to a second position when positioned outside the catheter lumen and collapses back to the first position within the catheter lumen when retracted back into the catheter lumen, where in use the plurality of electrodes are configured to substantially contact one or more portions of a pulmonary artery of a subject and to deliver a therapy signal to at least one autonomic fiber in proximity to the pulmonary artery to affect one or more of cardiac output and hemodynamics, wherein the therapy signal can, when in use, both increase heart contractility and affect heart contractility more than heart rate;
   a controller in electrical communication with one or more of the plurality of conductors and plurality of electrodes; and
   one or more sensors for measuring biological parameters and generating one or more sensor signals, the one or more sensors operationally connected to the controller, wherein the biological parameters comprise one or more of arterial blood pressure, central venous pressure, capillary pressure, systolic pressure variation, arterial blood gases, cardiac output, systemic vascular resistance, pulmonary artery wedge pressure, and mixed venous oxygen saturation, wherein the controller adjusts the therapy signal delivered by the therapy delivery device in response to the one or more sensor signals.

2. The device of claim 1, wherein the plurality of electrodes serve as cathodes and the collapsible frame serves as an anode.

3. The device of claim 1, wherein the collapsible frame comprises a superelastic material.

4. The device of claim 3, wherein the superelastic material comprises nitinol.

5. The device of claim 1, wherein the frame comprises an open stent-like configuration at a distal end.

6. The device of claim 5, wherein the configuration comprises diamond shapes connected to each other the connectors, sufficient to create the closed circular loop.

7. The device of claim 1, wherein the frame is capable of delivering a bioactive agent prior to, concurrent with or subsequent to electrical modulation.

8. The device of claim 7, where the controller operates one or more drug ports for delivery of bioactive agents.

9. The device of claim 1, wherein the at least one autonomic fiber comprises at least one of sympathetic fibers and parasympathetic fibers.

10. The device of claim 9, wherein the sympathetic fibers comprise one or more of right sympathetic nerves and left sympathetic nerves.

11. The device of claim 10, wherein the right sympathetic nerves comprise one or more of right dorsal medial cardiopulmonary nerves and right dorsal lateral cardiopulmonary nerves.

12. The device of claim 10, wherein the left sympathetic nerves comprise one or more of left ventral cardiopulmonary nerves, left dorsal medial cardiopulmonary nerves, left dorsal lateral cardiopulmonary nerves and left stellate cardiopulmonary nerves.

13. The device of claim 1, wherein each of the plurality of electrodes is annularly disposed on one of the plurality of insulated electrical conductors.

14. A therapy delivery device for treating cardiovascular medical conditions, the therapy delivery device comprising:
   a plurality of insulated electrical conductors each having a distal end;
   a plurality of electrodes, each said electrode of the plurality of electrodes being in electrical communication with one said insulated electrical conductor of the plurality of insulated electrical conductors, the plurality of electrodes being configured to contact one or more portions of a pulmonary artery of a subject and configured to deliver a therapy signal to at least one autonomic fiber proximate to the pulmonary artery to affect one or more of cardiac output and hemodynamics; and
   a frame connected to the distal ends of the plurality of insulated electrical conductors at a plurality of coupling points, the frame changeable between a first collapsed configuration in a catheter lumen and a second expanded configuration out of the catheter lumen, the plurality of electrodes proximal to the coupling points.

15. The device of claim 14, further comprising:
   a controller in electrical communication with the plurality of electrodes; and
   a sensor configured to measure a biological parameter and to generate sensor signals receivable by the controller.

16. The device of claim 15, wherein the biological parameter comprises one or more of arterial blood pressure, central venous pressure, capillary pressure, systolic pressure variation, arterial blood gases, cardiac output, systemic vascular resistance, pulmonary artery wedge pressure, and mixed venous oxygen saturation.

17. The device of claim 16, wherein the controller is configured to adjust the therapy signal delivered by the therapy delivery device in response to the sensor signals.

18. The device of claim 14, wherein the plurality of electrodes is spaced from a proximal end of the frame by segments of the plurality of insulated electrical conductors.

19. The device of claim 14, wherein the plurality of electrodes is proximate to a proximal end of the frame.

20. The device of claim 14, wherein each of the plurality of electrodes is annularly disposed on one of the plurality of insulated electrical conductors.

* * * * *